United States Patent [19]
Wilson et al.

[11] Patent Number: 5,990,033
[45] Date of Patent: Nov. 23, 1999

[54] SYNDIOTACTIC PROCHIRAL OLEFIN POLYMERIZATION USING NON-AROMATIC, ANIONIC, DIENYL GROUP CONTAINING COMPLEXES

[75] Inventors: David R. Wilson; Greg F. Schmidt, both of Midland, Mich.

[73] Assignee: The Dow Chemical Company, Midland, Mich.

[21] Appl. No.: 08/990,182

[22] Filed: Dec. 12, 1997

Related U.S. Application Data

[63] Continuation of application No. 08/345,048, Nov. 23, 1994, abandoned.

[51] Int. Cl.$^6$ .............................. B01J 31/00; B01J 37/00; C08F 4/02; C08F 4/60
[52] U.S. Cl. .................. 502/103; 502/113; 502/117; 502/152; 502/155; 526/160; 526/943
[58] Field of Search ............................. 502/103, 113, 502/117, 152, 155

[56] References Cited

U.S. PATENT DOCUMENTS

| | | |
|---|---|---|
| 3,242,099 | 3/1966 | Manyik et al. . |
| 4,774,301 | 9/1988 | Campbell, Jr. et al. . |
| 4,808,680 | 2/1989 | Schmidt et al. . |
| 4,871,704 | 10/1989 | Kohara et al. ............... 502/114 |
| 5,045,517 | 9/1991 | Campbell, Jr. et al. . |
| 5,064,802 | 11/1991 | Stevens et al. . |
| 5,064,918 | 11/1991 | Malanga . |
| 5,066,741 | 11/1991 | Campbell, Jr. . |
| 5,075,394 | 12/1991 | McDaniel et al. ............ 502/103 |
| 5,075,426 | 12/1991 | Zielinski ..................... 534/15 |
| 5,153,157 | 10/1992 | Hlatky et al. . |
| 5,198,401 | 3/1993 | Turner et al. . |
| 5,200,379 | 4/1993 | McDaniel et al. ............ 502/117 |
| 5,206,197 | 4/1993 | Campbell, Jr. . |
| 5,296,433 | 3/1994 | Siedle et al. . |
| 5,369,196 | 11/1994 | Matsumoto et al. . |
| 5,399,635 | 3/1995 | Neithamer et al. . |
| 5,470,993 | 11/1995 | Devore et al. . |
| 5,486,632 | 1/1996 | Devore et al. ............... 502/103 |
| 5,495,036 | 2/1996 | Wilson et al. ............... 502/103 |
| 5,539,068 | 7/1996 | Devore et al. ............... 502/103 |
| 5,541,349 | 7/1996 | Wilson et al. ............... 502/117 |
| 5,543,480 | 8/1996 | Patton et al. ................ 502/152 |
| 5,616,664 | 4/1997 | Timmers et al. ............. 502/103 |
| 5,679,816 | 10/1997 | Timmers et al. ............. 502/103 |
| 5,700,748 | 12/1997 | Murray ........................ 502/117 |
| 5,770,538 | 6/1998 | Devore et al. ............... 502/103 |
| 5,817,849 | 10/1998 | Wilson et al. ............... 502/103 |
| 5,886,117 | 3/1999 | Campbell, Jr. ............... 526/134 |
| 5,892,076 | 4/1999 | Nickias ........................ 502/117 |

FOREIGN PATENT DOCUMENTS

| | | |
|---|---|---|
| 277003 | 8/1988 | European Pat. Off. . |
| 468651 | 1/1992 | European Pat. Off. . |
| 520732 | 12/1992 | European Pat. Off. . |
| 2 488 259 | 2/1982 | France ..................... 502/152 |
| 8-81516 | 3/1996 | Japan . |
| WO 96/08498 | 3/1996 | WIPO . |

OTHER PUBLICATIONS

D. Devore et al., Organometallics, vol. 14, pp. 3132–3134, 1995.
Organometallics, Yamamoto, et al., 8, p. 105, 1989.
Organometallics, Blenkers, J., et al., 6, p. 459, 1987.
J. Am. Chem. Soc., 107, p. 5016, 1985 L. Spahl et al.
J. Am. Chem. Soc., 104, p. 3737, 1982, R.D. Ernst et al.
Chem. Rev., R. D. Ernst, 88, 1255–1291, 1988.
J. Chem. Soc. Chem. Comm., pp. 383–384, 1993 J. B. Lambert et al.
Organometallics, Lambert, J. B., et al., 13, pp. 2430–2443, 1994.
Angew. Chem. Int. Ed. Engl., 27, p. 1100, 1988, R.D. Ernst et al.
Organometallics, 6, pp. 1947–1954, 1987, P. DiMauro et al.

*Primary Examiner*—Mark L. Bell
*Assistant Examiner*—J. Pasterczyk

[57] ABSTRACT

Compositions comprising Group 4 metal complexes in the +2 or +3 formal oxidation state and containing an anionic pentadienyl ligand or a substituted derivative thereof and activating cocatalysts are used as catalysts for polymerizing olefins, diolefins and/or acetylenically unsaturated monomers. Monovinylidene aromatic monomers in particular are polymerized to form highly syndiotactic polymers.

5 Claims, No Drawings

SYNDIOTACTIC PROCHIRAL OLEFIN POLYMERIZATION USING NON-AROMATIC, ANIONIC, DIENYL GROUP CONTAINING COMPLEXES

This application is a Continuation of prior application Ser. No: 08/345,048 filed Nov. 23, 1994, abandoned.

BACKGROUND OF THE INVENTION

This invention relates to a process for preparing polymers of prochiral olefins, especially vinylaromatic monomers, having a high degree of syndiotacticity. More particularly, the invention relates to such a polymerization process using catalysts comprising certain Group 4 metal complexes in combination with one or more activating cocatalysts, characterized in that the complex comprises a cyclic or noncyclic, non-aromatic, anionic, dienyl ligand group forming a π-bond to the metal. In the complexes, the metal is in the +2 or +3 formal oxidation state.

It is previously known in the art to prepare highly syndiotactic vinyl aromatic polymers and other prochiral olefins by the use of titanium complexes containing a single cyclopentadienyl or substituted cyclopentadienyl group and an activating cocatalyst including alkylalumoxanes, inert, non-coordinating ion forming compounds, Lewis acids and mixtures thereof. Disclosures of such prior art processes are found in U.S. Pat. Nos. 5,045,517, 5,066,741, 5,206,197 and U.S. Pat. No. 5,886,117.

Bis(cyclopentadienyl)titanium complexes in which the titanium is in the +4 formal oxidation state, and olefin polymerization catalysts formed from such by combination with an activating agent, e.g., alumoxane or ammonium borate, are well known in the art. Thus, U.S. Pat. No. 3,242,099 described the formation of olefin polymerization catalysts by the combination of bis(cyclopentadienyl) titanium dihalides with alumoxane. U.S. Pat. No. 5,198,401 disclosed tetravalent bis(cyclopentadienyl)titanium complexes, including at col. 9, lines 24–27, diene-containing complexes and olefin polymerization catalysts obtained by converting such complexes into cationic form. Particularly preferred catalysts are obtained by the combination of ammonium borate salts with the bis(cyclopentadienyl) titanium complexes. Generally, such bis(cyclopentadienyl) containing complexes are inferior for use in catalysts to prepare polymers having a high degree of syndiotacticity.

The preparation of certain Ti, Zr, and Hf monocyclopentadienyl diene complexes was also described in Yamamoto et al., *Organometallics*, 8, 105 (1989) (Yamamoto) and Blenkers, J, et al., *Organometallics*, 6, 459 (1987) (Blenkers). Titanium and zirconium complexes in which the titanium is in the +4 formal oxidation state, including monocyclopentadienyl complexes are also known in the art. Examples of the foregoing references include: U.S. Pat. Nos. 5,064,918, 4,774,301, and 4,808,680.

In copending application, Ser. No. 08/082,197 filed Jun. 24, 1993, now abandoned, there are disclosed monocyclopentadienyl complexes having a cyclic structure in which the titanium is in the +2 formal oxidation state. The application also teaches the formation of olefin polymerization catalysts from such complexes by the combination of the complex with activator compounds such as alumoxanes, borate salts and strong Lewis acids. The teachings of all of the foregoing patents, patent applications and publications are hereby incorporated by reference.

SUMMARY OF THE INVENTION

According to the present invention there are provided compositions of matter useful as addition polymerization catalysts comprising:

A)
1) at least one metal complex corresponding to the formula:

$$Cp_mMP'_dX_pL_q$$

wherein:

M is titanium, zirconium or hafnium in the +2 or +3 formal oxidation state;

Cp is a group containing an anionic, cyclic, delocalized aromatic π-system through which the group is bound to M;

P' is a cyclic or noncyclic, non-aromatic, anionic, dienyl or allyl ligand group, bound to M through delocalization of said dienyl or allyl functionality, optionally said dienyl or allyl ligand group may be substituted with one or more groups independently selected from hydrocarbyl, silyl, hydrocarbyloxy, siloxy, germyl, halo, cyano, halohydrocarbyl and combinations thereof, said P' group containing up to 60 nonhydrogen atoms;

L independently each occurrence is a neutral ligating compound having up to 20 nonhydrogen atoms, with the proviso that L is not bound to M through an arene group or through a diene group;

X independently each occurrence is a monovalent anionic moiety having up to 20 non-hydrogen atoms, provided however that in no occurrence is X an aromatic or nonaromatic anionic group that is π-bonded to M;

alternatively, two X groups together may form a divalent, dianionic moiety having both valences bound to M, or alternatively, one or more X groups may be bonded to one or more L groups thereby forming a moiety that is both covalently bonded to M and coordinated thereto by means of Lewis base functionality;

m is 0 or 1;

d is 1 or 2;

p is 0, 1 or 2; and the sum of m, d and p is equal to the formal oxidation state of M;

q is 0, 1 or 2; and 2) an activating cocatalyst, the molar ratio of 1) to 2) being from 1:10,000 to 100:1; or B) the reaction product formed by converting 1) to an active catalyst by use of an activating technique.

Additionally according to the present invention there is provided a polymerization process for preparing polymers having a high degree of syndiotacticity comprising contacting one or more prochiral olefin monomers with a catalyst comprising the above defined composition of matter.

The present catalysts retain high efficiency over a wide range of polymerization conditions. In addition, the complexes are compatible with and may be used in combination with alkylaluminum compounds which may be employed to scavenge monomer impurities without detrimental effect to their catalytic properties. In particular the complexes have been found to be suitable for use in combination with various activating cocatalysts for the preparation of olefin polymers, especially monovinylidene aromatic polymers, that are highly syndiotactic.

The metal complexes of the present invention may be formed by reacting a metal precursor compound lacking the present P' group and containing one or two leaving groups, with a cyclic or noncyclic, non-aromatic dienyl-, allyl-, substituted dienyl-, or substituted dienyl- containing compound, optionally in the presence of a reducing agent. Suitable leaving groups include halide, hydrocarbyloxy, siloxy, sulfonate and carboxylate leaving groups. The procedure is analogous to those disclosed in *J. Am. Chem. Soc.*

107, 5016 (1985) or *Angew. Chem., Intr. Ed. Engl.,* 27, 1099 (1988) and *J. Am. Chem. Soc.,* 104, 3737 (1982). Optionally, if the metal, M, is initially in a higher formal oxidation state than desired in the resulting complex, the above reaction may be conducted in the presence of a reducing agent, or the metal precursor compound and reducing agent can first be contacted followed by addition of the cyclic or noncyclic, non-aromatic, anionic dienyl-, allyl-, substituted dienyl-, or substituted dienyl-containing compound. One or more neutral ligating compounds such as phosphines, phosphites, amines, carbon monoxide, or ethers may be present during the reaction or may be added later.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

The group, P' preferably does not decompose under reaction conditions used to prepare the complexes used in this invention. Under subsequent polymerization conditions, or in the formation of catalytic derivatives of the present complexes, P' may undergo chemical reactions or may be replaced by another ligand.

By the term "aromatic" when used with reference to Cp groups, is meant that the atoms contributing electrons to the π-system through which this anionic ligand is π-bonded to the metal form a cyclic, planar, π-system with 4n+2 electrons, where n is an integer greater than or equal to 0. Examples of suitable Cp groups include cyclopentadienyl, pyrroyl, cyclooctatetraenyl, and substituted derivatives thereof. Suitable substituents include hydrocarbyl, halocarbyl, halohydrocarbyl, silyl, germyl, halo, amino, phosphino, hydrocarbyloxy, siloxy and combinations thereof, said substituent having up to 20 nonhydrogen atoms, or optionally, two such substituents (except cyano or halo) are joined together causing Cp to have a fused ring structure. Examples of the latter fused ring structures include indenyl, fluorenyl, and hydrogenated derivatives thereof. Desirably, such Cp groups contain up to 50 non-hydrogen atoms.

Preferred Cp groups correspond to the formula:

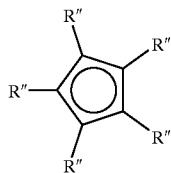

wherein:

R" in each occurrence is independently selected from the group consisting of hydrogen, hydrocarbyl, silyl, germyl, and combinations thereof said R" having up to 20 nonhydrogen atoms, or adjacent R" groups together form a hydrocarbylene group of up to 10 carbons which is connected to adjacent positions of the cyclopentadienyl ring. Most preferred Cp groups are selected from the group consisting of cyclopentadienyl, methylcyclopentadienyl, tetramethylcyclopentadienyl, pentamethylcyclopentadienyl, t-butylcyclopentadienyl, trimethylsilylcyclopentadienyl, indenyl, tetrahydroindenyl, fluorenyl, tetrahydrofluorenyl and octahydrofluorenyl.

Preferably, M is titanium or zirconium, most preferably titanium.

By the term "non-aromatic" when used with reference to P' groups is meant that the atoms contributing electrons to the π-system through which the anionic ligand is π-bonded to the metal do not form a cyclic, planar, π-system with 4n+2 electrons, where n is an integer greater than or equal to 0. Examples of suitable P' groups include pentadienyl, cyclohexadienyl, silacyclohexadienyl, cycloheptadienyl, or cyclooctadienyl groups, or substituted derivatives thereof, as well as the diphenyl/methyl group:

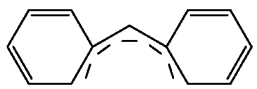

and partially hydrogenated or inertly substituted derivatives thereof. In the foregoing and other formulas herein, a delocalized negative charge is indicated by dots.

Inasmuch as the complexes can contain at most one anionic, cyclic, aromatic, π-bonded group, it follows that P' or X, singly or in combination, cannot comprise a cyclic, aromatic, π-bonded group, such as cyclopentadienyl, indenyl, fluorenyl, and hydrogenated derivatives thereof).

Preferred P' groups correspond to the following formulas:

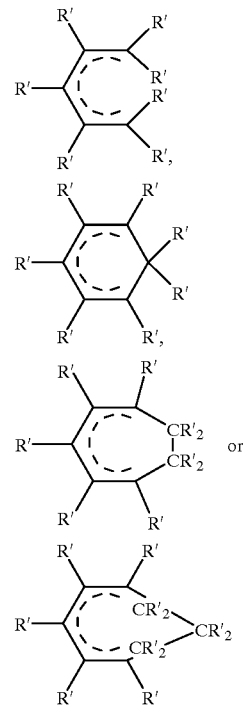

wherein:

R' in each occurrence is a ligand that is independently selected from the group consisting of hydrogen, hydrocarbyl, silyl, germyl, siloxy, amino, hydrocarbyloxy, cyano, halo and combinations thereof, said R' having up to 20 non-hydrogen atoms, and optionally, two or more R' groups (where R' is not hydrogen, halo or cyano) may together form a divalent derivative of one of the foregoing ligands.

Especially suitable P' groups are selected from the group consisting of pentadienyl, cyclohexadienyl, silacyclohexadienyl, cycloheptadienyl, or cyclooctadienyl groups; hydrocarbyl, silyl, hydrocarbyloxy and siloxy substituted derivatives of such groups; partially hydrogenated anthracenyl, or partially hydrogenated naphthalenyl groups; and hydrocarbyl, silyl, hydrocarbyloxy or siloxy substituted derivatives of such partially hydrogenated anthracenyl or partially hydrogenated naphthalenyl groups.

The P' group is bound to the metal atom by any suitable electronic interaction. In certain circumstances the exact form of electronic interaction may be indeterminate, because any one of several isomeric configurations thereof may be generated, that is, either $n^1$-, $n^3$-, or $n^5$-bonded P' ligands. This fact has been previously disclosed in the art, particularly in the teachings of R. D. Ernst, *Chem. Rev.*, 88, 1255–1291 (1988), and R. D. Ernst, et al., *J. Am. Chem. Soc.*, 107, 5016–5018 (1985). Moreover it is further well understood that the dienyl ligand in an $n^5$-bonded configuration may be depicted in every one of several isomeric configurations, known as the "W", "U" and "S" configurations. Such isomeric forms are illustrated with the 2,4-dimethylpentadienyl ligand in the following drawing:

"$\eta^1$"

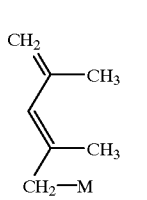

"$\eta^3$"

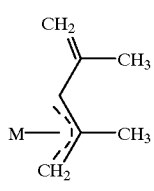

"$\eta^5$-W"

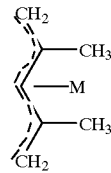

"$\eta^5$-U"

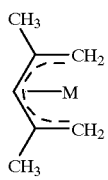

"$\eta^5$-S"

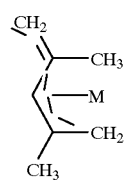

Such variants are not necessarily separately named herein nor are the carbon atoms contributing to the dienyl ligand's bonds always identified since the labile isomeric nature of such P' groups is well recognized by the skilled artisan, as illustrated by the above cited Ernst and Ernst, et al. references. It is to be further understood that in naming the foregoing P' groups, the original positions of the double bonds of the dienyl ligand need not be identified since in the final delocalized ligand group the original double bonds no longer exist, that is, the $n^5$-1,3-pentadienyl group is identical to the $n^5$-1,4-pentadienyl group. All such isomers are equivalent and may be referred to simply as $n^5$-pentadienyl. For purposes of the present invention it is to be understood that all possible isomeric forms of P' with regard to any reference to $n^1$, $n^3$, $n^5$ bonding or "W", "S", or "U" configurations are included in any reference to a specific isomer or electronic structure.

The positional numbering of the P' group herein is accomplished by identifying the carbons contributing to the π-bond or where no ambiguity is possible, merely identifying the total carbons contributing to such bond with the symbol, n. In monocyclic systems the lowest ordinals in sequence are assigned to the carbons contributing to the π-bond with the positions otherwise numbered so as to produce the lowest positional numbers for substituted carbon atoms. Thus, the trimethyl-substituted cyclohexadienyl ligand group derived from 1,5,5-trimethyl-1,3-cyclohexadiene (illustrated as follows)

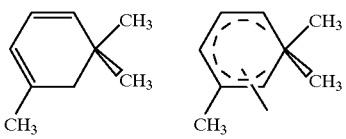

is named (2,6,6-trimethyl-n5-cyclohexadienyl) rather than (4,6,6-trimethyl-n5-cyclohexadienyl) or (1,1,2-trimethyl-n5-cyclohexadienyl). Multicyclic systems are numbered using standard nomenclature so as to avoid confusion. Specifically, hydrogenated naphthalenyl and hydrogenated anthracenyl systems are specifically illustrated as follows:

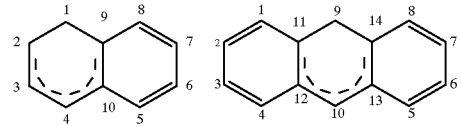

Hydrogenated positions of multicyclic systems are generally identified herein, however it is to be further understood that the various isomeric forms of such hydrogenated ligands, where possible, are not necessarily separately named herein.

Examples of the foregoing P' groups include: ($n^5$-pentadienyl), (2,4-dimethyl-$n^5$-pentadienyl), (1,5-dimethyl-$n^5$-pentadienyl), (1,5-bis(trimethylsilyl)-$n^5$-pentadienyl), ($n^5$-cyclohexadienyl), (6,6-dimethyl-$n^5$-cyclohexadienyl), (6,6-dimethyl-$n^5$-6-sila-cyclohexadienyl), (6-t-butyl-6-methoxy-$n^5$-6-sila-cyclohexadienyl), (6-methyl-6-fluoro-$n^5$-6-sila-cyclohexadienyl), (1, 2, 6, 6-tetramethyl-$n^5$-cyclohexadienyl), (1, 2, 4, 6, 6-pentamethyl-$n^5$-cyclohexadienyl), (1, 2, 5, 6, 6-pentamethyl-$n^5$-cyclohexadienyl), (1, 2, 4, 5, 6, 6-hexamethyl-$n^5$-cyclohexadienyl), (1, 2, 4, 5-tetramethyl-6, 6-cyclotrimethylene-$n^5$-cyclohexadienyl), (2, 3, 4, 9, 10-η-1, 2-dihydronaphthalenyl), (2, 3, 4, 9, 10-η-1, 2-dihydronaphthalenyl), (1, 1-dimethyl-2, 3, 4, 9, 10-η-1, 2-dihydronaphthalenyl), (1, 1-dimethyl-2, 3, 4, 9, 10-η-1, 2-dihydronaphthalenyl), diphenylmethyl, diphenyltrimethylsilylmethyl, di(1-cyclohexenyl)methyl, the equivalent ligands: (1, 1-dimethyl-2, 3, 4, 9, 10-η-1, 2, 5, 6, 7, 8-hexahydronaphthalenyl), (1, 1-dimethyl-2, 3, 4, 9, 10-η-1, 4, 5, 6, 7, 8-hexahydronaphthalenyl), and (1, 1-dimethyl-2, 3, 4, 9, 10η-1, 5, 6, 7, 8, 9-hexahydronaphthalenyl), the equivalent ligands (1, 1, 2, 3-tetramethyl-2, 3, 4, 9, 10-η-1, 2, 5, 6, 7, 8-hexahydronaphthalenyl), (1, 1, 2, 3-tetramethyl-2, 3, 4, 9, 10-η-1, 4, 5, 6, 7, 8-hexahydronaphthalenyl), and (1, 1, 2, 3-tetramethyl-2, 3, 4, 9, 10-η-1, 5, 6, 7, 8, 9-hexahydronaphthalenyl), (10, 11, 12, 13, 14-η-9, 10-dihydroanthracenyl), (9, 9-dimethyl-10, 11, 12, 13, 14-η-9, 10-dihydroanthracenyl), (10, 11, 12, 13, 14-η-1, 2, 3, 4, 9, 10-hexahydroanthracenyl), (10, 11, 12, 13, 14-η-1, 2, 3, 4, 9, 11-hexahydroanthracenyl), (10, 11, 12, 13, 14-η-1, 4, 5, 8, 9, 10-hexahydroanthracenyl), (9, 9-dimethyl-10, 11, 12, 13, 14-η-1, 4, 5, 8, 9, 10-hexahydroanthracenyl), (9, 9-dimethyl-10, 11, 12, 13, 14-η-1, 4, 5, 8, 9, 10-hexahydroanthracenyl), (8, 8-dimethyl-5, 6, 7, 13, 14-η-1, 4, 5, 8, 9,10-hexahydroanthracenyl), the equivalent ligands: (10, 11, 12, 13, 14-η-1, 2, 3, 4, 5, 6, 7, 8, 9,10-decahydroanthracenyl) and (10, 11, 12, 13, 14-η-1, 2, 3, 4, 5, 6, 7, 8, 9,11-decahydroanthracenyl); and the equivalent ligands: (9, 9-dimethyl-10, 11, 12, 13, 14-η-1, 2, 3, 4, 5, 6, 7, 8, 9,10-decahydroanthracenyl) and (9, 9-dimethyl-10, 11, 12, 13, 14-η-1, 2, 3, 4, 5, 6, 7, 8, 9,11-decahydroanthracenyl)

These groups are further illustrated in the following structures:

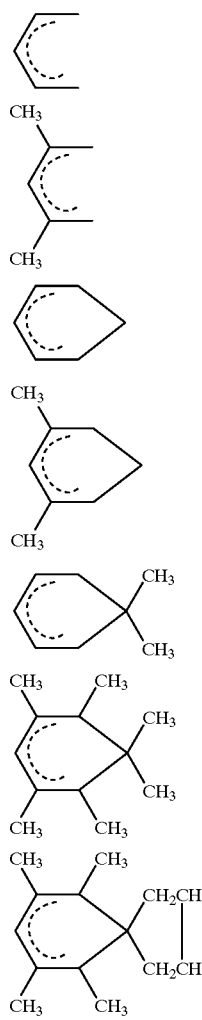

η⁵-pentalienyl), (2,4-dimethyl-η⁵-pentadienyl),

η⁵-cyclohexadienyl), (2,4-dimethyl-η⁵-cyclohexadienyl), (6,6-dimethyl-η⁵-cyclohexadienyl), (1,2,4,5,6,6-hexamethyl-η⁵-cyclohexadienyl), (1,2,4,5-tetramethyl-6,6-cyclotetramethylene-η⁵-cyclohexadienyl),

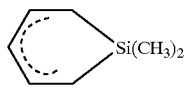 (6,6-dimethyl-η⁵-6-silacyclohexadienyl),

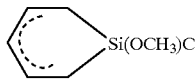 (6-t-butyl-6-methoxy-η⁵-6-silacyclohexadienyl),

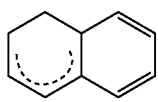 (2,3,4,9,10-η-1,2-dihydronaphthalenyl) or (1,2,3,9,10-η-1,4-dihydronaphthalenyl),

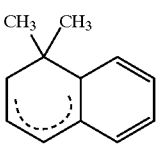 (1,1-dimethyl-2,3,4,9,10-η-1,2-dihydronaphthalenyl),

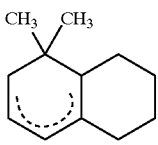 (1,1-dimethyl-2,3,4,9,10-η-1,4,5,6,7,8-hexahydronaphthalenyl), (1,1-dimethyl-2,3,4,5,10-η-1,2,6,7,8,9-hexahydronaphthalenyl), (1,1-dimethyl-3,4,5,6,10-η-1,2,3,7,8,9-hexahydronaphthalenyl),

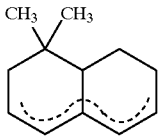 (1,1,2,3-tetramethyl-2,3,4,9,10-η-1,4,5,6,7,8-hexahydronaphthalenyl),

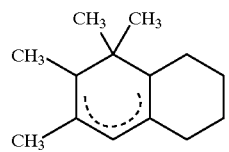 diphenylmethyl,

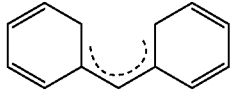 di(1-cyclohexenyl)methyl,

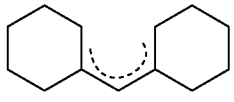 diphenyl(trimethylsilyl)methyl,

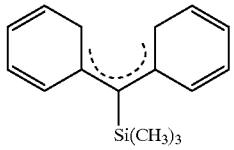 (10,11,12,13,14-η-9,10-dihydroanthracenyl),

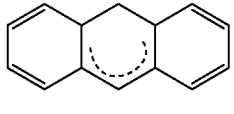 (9,9-dimethyl-10,11,12,13,14-η-9,10-dihydroanthracenyl),

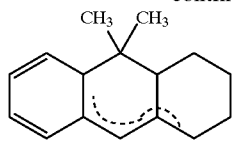 (9,9-dimethyl-4,10,12,13,14-η-1,2,3,4,9,10-hexahydroanthracenyl) or (9,9-dimethyl-4,10,12,14-η-1,2,3,4,9,11-hexahydroanthracenyl),

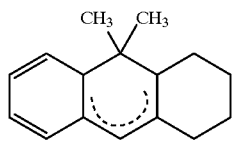 (9,9-dimethyl-10,11,12,13,14-η-1,2,3,4,9,10-hexahydroanthracenyl) or (9,9-dimethyl-10,11,12,13,14-η-1,2,3,4,9,11-hexahydroanthracenyl),

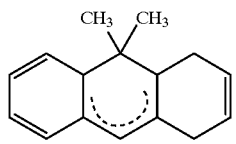 (9,9-dimethyl-10,11,12,13,14-η-1,4,5,8,9,10-hexahydroanthracenyl) or (9,9-dimethyl-10,11,12,13,14-η-1,4,5,8,9,11-hexahydroanthracenyl),

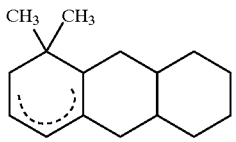 (1,1-dimethyl-2,3,4,11,12-η-1,4,5,6,7,8,9,10,13,14-decahydroanthracenyl) or (1,1-dimethyl-2,3,4,11,12-η-1,5,6,7,8,9,10,11,13,14-decahydroanthracenyl),

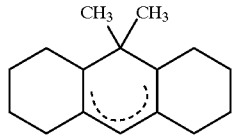 (9,9-dimethyl-10,11,12,13,14-η-1,2,3,4,5,6,7,8,9,10-decahydroanthracenyl) or (9,9-dimethyl-10,11,12,13,14-η-1,2,3,4,5,6,7,8,9,11-hexahydroanthracenyl)

Suitable X groups include both σ-bonded and π-bonded anionic ligands, excluding those of the class defined by Cp or P'. Examples of X groups include: halide (fluoride, chloride, bromide and iodide, especially chloride), hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)phosphino-substituted derivatives thereof, said X group having up to 20 nonhydrogen atoms. Preferred X groups are chloride, OR, and NR$_2$, where R independently each occurrence is a hydrocarbyl or silyl group of up to 10 nonhydrogen atoms. Especially suited X groups are methoxy, phenoxy, isopropoxy, and dimethylamido.

Preferred L groups are phosphines, especially trimethylphosphine, triethylphosphine, triphenylphosphine, trifluorophosphine and bis(1,2-dimethylphosphino)ethane; phosphites, especially trimethyl phosphite, triethyl phosphite, and dimethylphenyl phosphite; ethers, especially tetrahydrofuran; amines, especially pyridine, bipyridine, tetramethylethylenediamine (TMEDA), and triethylamine; and carbon monoxide.

Preferred coordination complexes used according to the present invention are complexes corresponding to the formula:

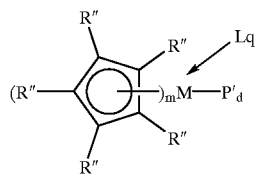

wherein:
M is titanium or zirconium in the +2 formal oxidation state;
L is a phosphine or a phosphite group having up to 15 nonhydrogen atoms;
R" is as previously defined;
P' is pentadienyl, cyclohexadienyl, 6,6-dimethylcyclohexadienyl, silacyclohexadienyl, diphenylmethyl, diphenyl(trimethylsilyl)methyl or 2,4-dimethylpentadienyl;
m, and d are as previously defined, and
q is 0 or 1.

More preferably, R" independently in each occurrence is hydrogen, methyl, ethyl, propyl, butyl, pentyl, hexyl, (including where appropriate all isomers), cyclopentyl, cyclohexyl, norbornyl, benzyl, phenyl, silyl of up to 5 nonhydrogen atoms, or adjacent R" groups are linked together thereby forming an indenyl, tetrahydroindenyl, fluorenyl, tetrahydro-fluorenyl, or octahydro-fluorenyl group.

Most preferred coordination complexes used according to the present invention are complexes corresponding to the formula:

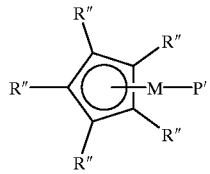

wherein:
M is titanium in the +2 formal oxidation state;
R" is hydrogen or methyl; and
P' is pentadienyl, 6,6-dimethylcyclohexadienyl, diphenylmethyl, diphenyltrimethylsilylmethyl or 2,4-dimethylpentadienyl.

In general, the complexes can be prepared by combining a compound corresponding to the P' group of the resulting complex, a Group 4 metal compound and optional reducing agent, as previously described, in a suitable noninterfering solvent at a temperature from –100° C. to 300° C., preferably from –78 to 100° C., most preferably from 0 to 80° C. By the term "reducing agent" herein is meant a metal or compound which, under reducing conditions causes the metal center of the resulting complex to be reduced to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes are aliphatic and aromatic hydrocarbons and halohydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, styrene and the like, $C_{1-4}$ dialkyl ethers, $C_{1-4}$ dialkyl ether derivatives of (poly)alkylene glycols, and tetrahydrofuran. Mixtures of the foregoing are also suitable.

The recovery procedure involves separation of the resulting alkali metal or alkaline earth metal salt and devolatilization of the reaction medium. Extraction into a secondary solvent may be employed if desired. Alternatively, if the desired product is an insoluble precipitate, filtration or other separation technique may be employed.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or diisobutylalumoxane; strong Lewis acids, such as, $C_{1-30}$ hydrocarbyl substituted Group 13 compounds, especially tri(hydrocarbyl)aluminum- or tri(hydrocarbyl)boron- compounds and halogenated derivatives thereof, having from 1 to 10 carbons in each hydrocarbyl or halogenated hydrocarbyl group, especially tris(pentafluorophenyl)borane; and nonpolymeric, inert, compatible, noncoordinating, ion forming compounds (including the use of such compounds under oxidizing conditions). A suitable activating technique is bulk electrolysis (explained in more detail hereinafter). Combinations of the foregoing activating cocatalysts and techniques may also be employed if desired. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651 (equivalent to U.S. Ser. No. 07/547,718, abandoned), EP-A-520,732 (equivalent to U.S. Ser. No. 07/876,268 now U.S. Pat. No. 5,721,185), and EP-A-520,732 (equivalent to U.S. Ser. Nos. 07/884,966 filed May 1, 1992 now U.S. Pat. No. 5,350,723), the teachings of which are hereby incorporated by reference.

Suitable nonpolymeric, inert, compatible, noncoordinating, ion forming compounds useful as cocatalysts in one embodiment of the present invention comprise a cation which is a Bronsted acid capable of donating a proton, and an inert, compatible, noncoordinating, anion, $A^-$. Preferred anions are those containing a single coordination complex comprising a charge-bearing metal or metalloid core which anion is capable of balancing the charge of the active catalyst species (the metal cation) which is formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula: $(L^*-H)^+_f(A^{f-})$ wherein:
L* is a neutral Lewis base;
$(L^*-H)^+$ is a Bronsted acid;
$A^{f-}$ is a noncoordinating, compatible anion having a charge of f-, and
f is an integer from 1 to 3.

More preferably f is one, that is $A^{f-}$ is $A^-$. Highly preferably, $A^-$ corresponds to the formula: $[BQ_4]^-$
wherein:
B is boron in the +3 formal oxidation state; and
Q independently each occurrence is selected from hydride, dialkylamido, halide, alkoxide, aryloxide, hydrocarbyl, and halosubstituted-hydrocarbyl radicals, said Q having up to 20 carbons with the proviso that in not more than one occurrence is Q halide.

In a most preferred embodiment, Q is a fluorinated $C_{1-20}$ hydrocarbyl group, most highly preferably, a fluorinated aryl group, especially, pentafluorophenyl.

Illustrative, but not limiting, examples of ion forming compounds comprising proton donatable cations which may be used as activating cocatalysts in the preparation of the catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl(2,4,6-trimethylanilinium) tetrakis(pentafluorophenyl)borate, trimethylammonium tetrakis(2,3,4,6-tetrafluorophenylborate, triethylammonium tetrakis(2,3,4,6-tetrafluorophenyl)borate, tripropylammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethylanilinium tetrakis(2,3,4,6-tetrafluorophenyl)borate, N,N-diethylanilinium tetrakis(2,3,4,6-tetrafluorophenyl)borate, and N,N-dimethyl-(2,4,6-trimethylanilinium) tetrakis-(2,3,4,6-tetrafluorophenyl)borate; dialkyl ammonium salts such as: di-(i-propyl)ammonium tetrakis(pentafluorophenyl)borate, and dicyclohexylammonium tetrakis(pentafluorophenyl)borate; and tri-substituted phosphonium salts such as: triphenylphosphonium tetrakis(pentafluorophenyl)borate, tri(o-tolyl)phosphonium tetrakis(pentafluorophenyl)borate, and tri(2,6-dimethylphenyl)phosphonium tetrakis(pentafluorophenyl)borate.

Preferred are N,N-dimethylanilinium tetrakis(pentafluorophenyl)borate and tributylammonium tetrakis(pentafluorophenyl)borate.

Another suitable nonpolymeric, inert, compatible, noncoordinating, ion forming, activating cocatalyst comprises a salt of a cationic oxidizing agent and a noncoordinating, compatible anion represented by the formula: $(Ox^{e+})_f(A^{f-})_e$
wherein:
$Ox^{e+}$ is a cationic oxidizing agent having a charge of e+;
e is an integer from 1 to 3; and
$A^{f-}$, and f are as previously defined.

Examples of cationic oxidizing agents include: ferrocenium, hydrocarbyl-substituted ferrocenium. $Ag^+$, or $Pb^{+2}$. Preferred embodiments of $A^{f-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula: $©^+A^-$
wherein:
$©^+$ is a $C_{1-20}$ carbonium ion; and
$A^-$ is as previously defined. A preferred carbonium ion is the trityl cation, i.e. triphenylcarbonium.

A further suitable ion forming, activating cocatalyst comprises a compound which is a salt of a silylium ion and a noncoordinating, compatible anion represented by the formula:

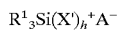

wherein:

R¹ is C₁₋₁₀ hydrocarbyl, h is a number from 0 to 3, and

X' and A⁻ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem.Comm.*, 1993, 383–384, as well as Lambert, J. B., et al., *Organometallics*, 1994, 13, 2430–2443. The use of the above silylium salts as activating cocatalysts for addition polymerization catalysts is claimed in U.S. patent application Ser. No. 08/304,314, filed Sep. 12, 1994, the teachings of which are hereby incorporated by reference.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433, the teachings of which are herein incorporated by reference.

The foregoing activating techniques and ion forming cocatalysts are also preferably used in combination with a tri(hydrocarbyl)aluminum compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

An especially preferred activating cocatalyst comprises the combination of a trialkyl aluminum compound having from 1 to 4 carbons in each alkyl group and an ammonium salt of tetrakis(pentafluorophenyl)borate, in a molar ration from 0.1:1 to 1:0.1, optionally containing up to 1000 mole percent of an alkylaluminoxane.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), DME, and mixtures thereof.

The electrolysis may be conducted in a standard electrolytic cell containing an anode and cathode (also referred to as the working electrode and counter electrode respectively). Suitably materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping he cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and an inert, compatible, noncoordinating anion, A⁻. Preferred supporting electrolytes are salts corresponding to the formula G⁺A⁻; wherein:

G⁺ is a cation which is nonreactive towards the starting and resulting complex, and A⁻ is a noncoordinating, compatible anion.

Examples of cations, G⁺, include tetrahydrocarbyl substituted ammonium or phosphonium cations having up to 40 nonhydrogen atoms. A preferred cation is the tetra-n-butylammonium cation.

During activation of the complexes of the present invention by bulk electrolysis the cation of the supporting electrolyte passes to the counter electrode and A⁻ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoro-aryl) berates having from 1 to 10 carbons in each hydrocarbyl group, especially tetra-n-butylammonium tetrakis(pentafluorophenyl) borate.

The molar ratio of catalyst/cocatalyst employed preferably ranges from 1:10,000 to 100:1, more preferably from 1:5000 to 10:1, most preferably from 1:10 to 1:1.

Preferred activating cocatalysts are methylalumoxane (MAO), C₁₋₁₀ trihydrocarbylammonium tetrakis (pentafluorophenyl)borate compounds, perfluorinated triarylborane compounds, or mixtures thereof.

The catalysts may be used to polymerize ethylenically and/or acetylenically unsaturated monomers having from 2 to 20 carbon atoms either alone or in combination. Preferred monomers include the C₂₋₁₀ α-olefins especially ethylene, propylene, isobutylene, 1-butene, 1-hexene, 3-methyl-1-pentene, 4-methyl-1 -pentene, and 1-octene and mixtures thereof. Other preferred monomers include monovinylidene aromatic monomers, especially styrene, C₁₋₄ alkyl substituted styrene, α-methylstyrene, and mixtures thereof; tetrafluoro-ethylene; vinylbenzocyclobutane; ethylidenenorbornene; 4-vinylcyclohexene; vinylcyclohexane; and 1,4-hexadiene. Mixtures of the foregoing monomers may also be polymerized.

In general, the polymerization may be accomplished at conditions well known in the prior art for Ziegler-Natta or Kaminsky-Sinn type polymerization reactions, i.e., temperatures from 0–250° C. and pressures from atmospheric to 10000 atmospheres. Suspension, solution, slurry, gas phase or other process conditions may be employed if desired. A support, especially silica, alumina, or a polymer (especially polytetrafluoroethylene or a polyolefin) may be employed, and desirably is employed when the catalysts are used in a slurry or gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}:1$ to $10^{-1}:1$, more preferably from $10^{-12}:1$ to $10^{-5}:1$.

Suitable solvents for polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and the like and aromatic and alkyl-substituted aromatic compounds such as benzene, toluene, xylene and the like. Suitable solvents also include liquid olefins which may act as monomers or comonomers including ethylene, propylene, butadiene, cyclopentene, 1-hexene, 1-hexane, 4vinylcyclohexane, vinylcyclohexane, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable.

When the present polymerization catalysts are used to polymerize prochiral olefins, especially monovinylidene aromatic monomers, syndiotactic or isotactic polymers are attainable. As used herein, the term "syndiotactic" refers to polymers having a stereoregular structure of greater than 50 percent, preferably greater than 75 percent syndiotactic of a racemic triad as determined by $^{13}C$ nuclear magnetic resonance spectroscopy. Conversely, the term "isotactic" refers to polymers having a stereoregular structure of greater than 50 percent, preferably greater than 75 percent isotactic of a racemic triad as determined by $^{13}C$ nuclear magnetic resonance spectroscopy. Such polymers may be usefully employed in the preparation of articles and objects via compression molding, injection molding or other suitable technique having an extremely high resistance to deformation due to the effects of temperature.

The catalysts may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent U.S. Ser. No. 07/904,770, as well as U.S. Ser. No. 08/10958, filed Jan. 29, 1993, the teachings or which are hereby incorporated by reference herein.

One such solution phase polymerization process comprises:

contacting in a solvent one or more α-olefins with a metal complex according to the present invention and one or more cocatalyst activators in one or more continuous stirred tank or tubular reactors connected in series or parallel, and recovering the resulting polymer.

In another such solution phase polymerization process, in one or more of the foregoing reactors, one or more α-olefins are also contacted with a catalyst composition comprising one or more metal complexes according to the present invention in admixture with one or more homogeneous metal complexes other than a complex according to the present invention, said catalyst composition also comprising one or more cocatalyst activators.

In yet another solution process an ethylene/α-olefin interpolymer composition is prepared by:

(A) contacting ethylene and at least one other α-olefin under solution polymerization conditions in the presence of a homogeneous catalyst composition comprising a metal complex of the present invention with at least one of the aforementioned activating cocatalysts in at least one reactor to produce a solution of a first interpolymer, (B) contacting ethylene and at least one other α-olefin under solution polymerization conditions and at a higher polymerization reaction temperature than used in step (A) in the presence of a heterogeneous Ziegler catalyst in at least one other reactor to produce a solution of a second interpolymer, and (C) combining the solution of the first interpolymer with the solution of the second interpolymer to form a solution comprising the ethylene/α-olefin interpolymer composition, and (D) recovering the ethylene/α-olefin interpolymer composition.

Preferably the heterogeneous Ziegler catalyst comprises:

(i) a solid support component comprising magnesium halide, silica, modified silica, alumina, aluminum phosphate, or a mixture thereof, and (ii) a transition metal component represented by the formula:

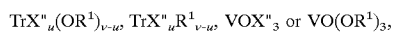

$$TrX''_u(OR^1)_{v-u}, TrX''_uR^1_{v-u}, VOX''_3 \text{ or } VO(OR^1)_3,$$

wherein:
Tr is a Group 4, 5, or 6 metal,
u is a number from 0 to 6 that is less than or equal to v,
v is the formal oxidation number of Tr,
X" is a halogen,
$R^1$ independently each occurrence is a hydrocarbyl group having from 1 to 20 carbon atoms.

These polymerizations are generally carried out under solution conditions to facilitate the intimate mixing of the two polymer-containing streams. The foregoing technique allows for the preparation of ethylene/α-olefin interpolymer compositions having a broad range of molecular weight distribution and composition distribution. Preferably, the heterogeneous catalyst is also chosen from those catalysts which are capable of efficiently producing the polymers under high temperature, especially, temperatures greater than or equal to 180° C. under solution process conditions.

In a still further embodiment, there is provided a process for preparing an ethylene/α-olefin interpolymer composition, comprising:

(A) polymerizing ethylene and at least one other α-olefin in a solution process under suitable solution polymerization temperatures and pressures in at least one reactor containing a catalyst composition comprising the metal complex of the present invention with at least one of the aforementioned activating cocatalysts to produce a first interpolymer solution, (B) passing the interpolymer solution of (A) into at least one other reactor containing a heterogeneous Ziegler catalyst, in the presence of ethylene and optionally one other α-olefin under solution polymerization conditions to form a solution comprising the ethylene/α-olefin interpolymer composition, and (C) recovering the ethylene/α-olefin interpolymer composition.

Preferably the heterogeneous Ziegler catalyst comprises:
(i) a solid support component comprising a magnesium halide or silica, and
(ii) a transition metal component represented by the formula:

$TrX''_u(OR^1OR)_{v-u}$, $TrX''_u R^1_{v-u}$, $VOX''_3$ or $VO(OR^1)_3$, wherein:

Tr, X'', u, v, and $R^1$ are as previously defined.

The foregoing technique also allows for the preparation of ethylene/α-olefin interpolymer compositions having a broad range of molecular weight distributions and composition distributions. Particularly desirable α-olefins for use in the foregoing processes are $C_{4-8}$ α-olefins, most desirably 1-octene.

The skilled artisan will appreciate that the invention disclosed herein may be practiced in the absence of any component which has not been specifically disclosed. The following examples are provided as further illustration thereof and are not to be construed as limiting. Unless stated to the contrary all parts and percentages are expressed on a weight basis.

EXAMPLE 1

Cyclopentadienyl(2,4-dimethylpentadienyl)titanium (II).P($C_2H_5$)$_3$

Preparation

This compound was prepared in a manner similar to that used by Ernst et al., *Angew. Chem. Int. Ed. Engl.*, 27, 1100 (1988). To a slurry of 1.13 g (6.14 mmole) cyclopentadienyl titanium dichloride in 50 mL tetrahydrofuran (THF) was added 6.20 mL of a 1.00 M (6.20 mmol) solution of triethylphosphine in THF with a concurrent color change of the slurry from blue to green. To this solution was then added 1.90 g (14.2 mmol) potassium 2,4-dimethylpentadienide in 35 mL THF. The reaction mixture was stirred overnight. The solvent was removed from the red-brown solution under reduced pressure and the residue was extracted with pentane and filtered. The dark red-orange solution was concentrated to dryness, then the resulting solid was triturated with pentane and cooled in the freezer. The solid was collected on a frit, washed two times with cold pentane and dried under reduced pressure. The yield of orange powder was 1.38 g, 68.8 percent. $^1$H NMR ($C_6D_6$) δ 6.02 (s, 1H), 5.02 (s, 5H), 1.84 (s, 8H), 1.27 (m, 6H), 0.72 (m, 9H), −0.84 (5, 2H).

The resulting complex had the formula:

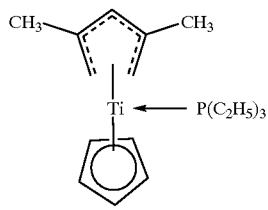

Polymerization

Cyclopentadienyl(2,4-dimethylpentadienyl)titanium.P($C_2H_5$)$_3$ (0.03 M in toluene), methylalumoxane (MAO) or dimethylanilinium tetrakispentafluorophenylborate (DMATB) (Cocatalyst (I), (2.0 M in toluene)), and optionally triisobutylaluminum (TIBA, 1.0 M in toluene) (cocatalyst II) were combined for one hour at 25° C. before addition to styrene (10 mL) in a sealed glass vial. The glass vial was sealed and heated to 70° C. for one hour. After this time the polymerization was quenched by addition of methanol and the polymer dried under reduced pressure. The resulting polymers possessed crystalline melting points in excess of 260° C., indicating that the polymers were syndiotactic. Results are contained in Table I.

TABLE I

| Run | Cocatalyst (I) | Cocatalyst (II) | Molar ratio Styrene/ Cocatalyst (I)/ Cocatalyst (II)/ catalyst | Yield (percent) |
|---|---|---|---|---|
| 1 | MAO | TIBA | 233,000/200/200/1 | 9.3 |
| 2 | " | — | 233,000/200/0/1 | 22.4 |

EXAMPLE 2

Pentamethylcyclopentadienyl(2,4-dimethylpentadienyl)titanium (II)

A solution of 2.78 g (20.7 mmol) of potassium 2,4-dimethylpentadienide in 50 mL THF was added dropwise to a solution of 2.00 g (6.91 mmol) of $C_5(CH_3)_5TiCl_3$ and 7.10 mL of a 1.00 M (7.10 mmol) THF solution of triethylphosphine in an additional 45 mL of THF. After the addition was complete, the reaction mixture was brownish-red. The reaction mixture was allowed to stir for approximately 16 hours. The solvent was removed under reduced pressure. The extremely dark, tar-like residue was extracted with hexane and filtered. The hexane was removed under reduced pressure from the dark yellow-brown solution to leave the product as an oil. A few milliliters of hexane were added, and black crystalline material was isolated after cooling about 14 hours in a −40° C. freezer. Yield was 0.234 g, 12.2 percent. $^1$H NMR ($C_6D_6$) δ 6.70 (s, 1H), 2.03 (d, 2H, J=5.5 Hz), 1.89 (s, 6H), 1.53 (s, 15H), 1.17 9d, 2H, J=5.0 Hz). $^{13}$C NMR ($C_6D_6$) δ 124.6, 122.6, 120.2, 78.9, 29.7, 11.4.

The product had the formula:

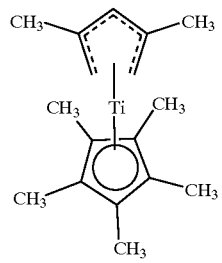

Polymerization

Pentamethylcyclopentadienyl (2,4-dimethylpentadienyl) titanium (II) and MAO cocatalyst were combined in toluene and added to styrene monomer in a sealed glass vial. The ratio of styrene/MAO/metal complex was 233,000/200/1. The polymerization was conducted under anaerobic conditions in a manner analogous to Run 2 of Example 1 except that the catalyst/cocatalyst solution was stirred for approximately 5 minutes at room temperature before addition to the styrene and the polymerization time was two hours. Yield of polymer was 34.3 percent. The resulting polymer possessed a crystalline melting point in excess of 260° C., indicating it was syndiotactic.

EXAMPLE 3

Bis(2,4-dimethylpentadienyl)titanium (II)

This complex was prepared in a manner similar to that disclosed in *J. Am. Chem. Soc.*, 104, 3737 (1982). A solution of 2.50 g (18.6 mmol) potassium 2,4-dimethylpentadienide in 50 mL THF was slowly added to a slurry of 2.30 g (6.21 mmol) TiCl$_3$.THF$_3$ in 50 mL THF. The reaction mixture was stirred for several days, then the solvent was removed and the residue extracted with pentane. After filtering, the product was isolated as an intensely dark green oil. The product was identified on the basis of its $^1$H NMR spectrum. Yield was 82.5 percent. Small quantities of coupled byproduct, tetramethyldecatetraene, were also present.

Polymerization

The polymerization conditions of Example 2 were substantially repeated using the bis(2,4-dimethylpentadienyl) titanium complex in combination with MAO cocatalyst and optionally TIBA. The resulting polymers possessed crystalline melting points in excess of 260° C., indicating that the polymers were highly syndiotactic. Molar ratios and results are contained in Table II.

TABLE II

| Run | Cocatalyst (I) | Cocatalyst (II) | Molar ratio Styrene/ Cocatalyst (I)/ Cocatalyst (II)/ catalyst | Yield (percent |
|---|---|---|---|---|
| 1 | MAO | TIBA | 233,000/200/200/1 | 0.8 |
| 2 | MAO | — | 233,000/200/0/1 | 1.3 |

EXAMPLE 4

Bis-6,6-dimethylcyclohexadienyl titanium (II)

This compound was prepared in a fashion similar to that reported in *Organometallics*, 6, 1947–1954 (1987). A solution of 0.60 g (4.10 mmol) potassium 6,6-dimethylcyclohexadienide in 50 mL THF was added dropwise at room temperature to a slurry of 0.51 g (1.37 mmol) TiCl$_3$.3THF in a solvent mixture of 15 mL THF and 125 mL diethylether. After stirring at room temperature for 8 hours the solvent was removed under reduced pressure to give dark solids. This solid was extracted with hexane and filtered to give a green solution. Removal of the hexane under reduced pressure gave a viscous green oil. Comparison to literature characterization confirmed the compound structure as follows:

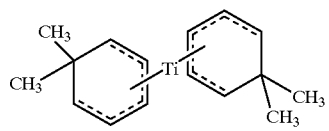

Polymerization

Bis(6,6-dimethylcyclohexadienyl)titanium (II) was used in combination with MAO cocatalyst to polymerize styrene monomer. The polymerization was conducted under anaerobic conditions in a manner analogous to Example 2. The ratio of styrene/MAO/metal complex was 233,000/200/1. Yield of polymer was 3.4 percent. The resulting polymer possessed a crystalline melting point in excess of 260° C., indicating that the polymer was highly syndiotactic.

EXAMPLE 5

Bis(diphenylmethyl)titanium (II)

1) Preparation of diphenylmethyl potassium

To a solution of 18.3 g (109 mmol) of diphenylmethane in 400 mL of hexane were added 12.0 g (109 mmol) of potassium t-amylate. To the resulting pale yellow solution were added 68.7 mL of 1.60 M (110 mmol) butyl lithium. The thick, bright orange slurry was stirred about 16 hours. The solids were collected on a filter, washed three times with 100 mL, then twice with 50 mL of hexane, then dried under reduced pressure. The yield of bright orange powder was 18.23 g, 81.2 percent.

2) Preparation of bis(diphenylmethyl)titanium (II)

A mixture of 0.21 g (8.90 mmol) of magnesium turnings and 1.00 g (2.70 mmol) of TiCl$_3$.3THF in about 50 mL of THF was stirred for several days to form TiCl$_2$. To this black slurry 1.11 g (5.40 mmol) of diphenylmethyl potassium was then added. The color changed rapidly to deep dark greenish orange indicating that a reaction took place. The mixture was stirred for approximately 15 hours. The solvent was removed under reduced pressure. The black residue was extracted with toluene and filtered and the toluene was removed under pressure. The black residue was redissolved in 20 mL of toluene, then precipitated with hexane. The product was dried under reduced pressure. The yield was 0.556 g, 53.9 percent.

Polymerization

The bis(diphenylmethyl)titanium (II) complex (0.01 M in toluene), MAO (1.6 M in toluene), dimethylanilinium tetrakispentafluorophenylborate (DMATB) (0.002 M in toluene), or tris(pentafluorophenyl)borane (borane) (0.01 M in toluene) were combined for about 5 minutes then added to styrene monomer or vinylcyclohexane (VCH) and sealed in a glass vial and heated to 70° C. for two hours. After this time the polymerization was quenched by addition of methanol and the polymer dried under reduced pressure. The resulting styrene polymers possessed crystalline melting points in excess of 260° C., indicating that the polymers were syndiotactic. Molar ratios of reactants and results are contained in Table III.

TABLE III

| Run | Monomer | Cocatalyst | Molar ratio Monomer/ Cocatalyst/ Catalyst | Yield (percent) |
|---|---|---|---|---|
| 1 | styrene | MAO | 50,000/1000/1 | 2.7 |
| 2 | " | borane | 50,000/1/1 | 1.4 |
| 3 | " | DMATB | 50,000/1/1 | 1.7 |
| 4 | VCH | MAO | 50,000/1000/1 | 1.6 |

EXAMPLE 6

Bis(diphenyltrimethylsilylmethyl) titanium (II)

1) Preparation of diphenyltrimethylsilylmethane

To a solution of 5.01 g (24.3 mmol) of diphenylmethyl potassium in 25 mL of THF was added about 10 mL (about 8.6 g, 80 mmol) of chlorotrimethylsilane. The dark orange color instantly faded. The solvent was removed under reduced pressure. The residue was extracted with hexane and filtered and the solvent was removed under pressure to give the product as a pale yellowish liquid. The yield was 4.63 g, 79.3 percent. 1H NMR (C$_6$D$_6$) δ 7.08–7.23 (m, 8H), 6.98–7.06 (m, 2H), 3.41 (s, 1H), 0.00 (s, 9H). $^{13}$C NMR (C$_6$D$_6$) δ 143.2, 129.1, 128.6, 125.4, 46.5, −1.4.

2) Preparation of diphenyltrimethylsilylmethyl potassium

To a solution of 4.55 g (18.9 mmol) of diphenyltrimethylsilylmethane in 100 mL of ether were added 11.8 mL of 1.60 M (18.9 mmol) n-butyl lithium to form an orange-brown solution. About half of the ether was removed under reduced pressure. About 50 mL of hexane were then added after which 2.09 g (18.9 mmol) of solid potassium t-amylate were added. The resulting orange slurry was stirred for approximately 16 hours. The solids were collected on a filter, washed with hexane, then dried under reduced pressure. The yield of bright orange powder was approximately 90 percent.

3) Preparation of bis(diphenyltrimethylsilylmethyl) titanium

A mixture of 0.310 g (12.8 mmol) of magnesium turnings and 1.00 g 92.7 mmol) of $TiCl_3 \cdot 3THF$ in about 70 mL of THF was stirred for several days to form $TiCl_2$. To this black slurry 1.50 g (5.40 mmol) of solid diphenyltrimethylsilylmethyl potassium was then added. The color changed rapidly to greenish orange indicating formation of the metal complex. The mixture was stirred for about two hours, then filtered and the solvent was removed under reduced pressure. The black residue was extracted with toluene, then filtered and the toluene was removed under reduced pressure. The black residue was then redissolved in 10 mL of toluene and precipitated with 100 mL of hexane. The resulting product was dried under reduced pressure, giving 0.610 g, 37.4 percent yield.

Polymerization

The polymerization conditions of Example 5 were substantially repeated using the bis(diphenyltrimethylsilylmethyl)titanium (II) complex (0.01 M in toluene), and MAO (1.6 M in toluene), dimethylanilinium tetrakispentafluorophenylborate (DMATB) (0.002 M in toluene), or tris(pentafluorophenyl)borane (borane) (0.01 M in toluene) cocatalyst. Styrene monomer, vinylcyclohexane (VCH) or 4-vinylcyclohexene (4-VCH) were polymerized. The resulting styrene polymers possessed crystalline melting points in excess of 260° C., indicating that the polymers were syndiotactic. Molar ratios of reactants and results are contained in Table IV.

TABLE IV

| Run | Monomer | Cocatalyst | Molar ratio Monomer/ Cocatalyst/ Catalyst | Yield (percent) |
|---|---|---|---|---|
| 1 | styrene | MAO | 50,000/1000/1 | 2.8 |
| 2 | " | borane | 50,000/1/1 | 1.5 |
| 3 | " | DMATD | 50,000/1/1 | 1.6 |
| 4 | VCH | MAO | 50,000/1000/1 | 1.6 |
| 5 | 4-VCH | MAO | 50,000/1000/1 | 1.6 |

What is claimed is:

1. A composition of matter comprising:

A)

1) at least one metal complex corresponding to the formula:

$$Cp_m MP'_d X_p L_q$$

wherein:

M is titanium, zirconium or hafnium in the +2 or +3 formal oxidation state;

Cp is a group containing an anionic, cyclic, delocalized aromatic π-system through which the group is bound to M;

P' is an ionic cyclic or noncyclic group containing up to 60 nonhydrogen atoms selected from the group consisting of: pentadienyl, cyclohexadienyl, silacyclohexadienyl, cycloheptadienyl, cyclooctadienyl, diphenylmethyl, partially hydrogenated anthracenyl, partially hydrogenated naphthalenyl groups, hydrocarbyl-, silyl-, hydrocarbyloxy-, and siloxy-substituted derivatives thereof;

L independently each occurrence is a neutral ligating compound having up to 20 nonhydrogen atoms, with the proviso that L is not bound to M through an arene group or through a diene group;

X independently each occurrence is a monovalent anionic moiety having up to 20 non-hydrogen atoms, provided however that in no occurrence is X an aromatic or non-aromatic anionic group that is π-bonded to M; alternatively, two X groups together may form a divalent, dianionic moiety having both valences bound to M, or alternatively, one or more X groups may be bonded to one or more L groups thereby forming a moiety that is both covalently bonded to M and coordinated thereto by means of a Lewis base functional group;

m is 0 or 1;

d is 1 or 2;

p is 0, 1 or 2; and the sum of m, d and p is equal to the formal oxidation state of M;

q is 0, 1 or 2; and 2) an activating cocatalyst which renders the metal complex catalytically active for addition polymerization, the molar ratio of 1) to 2) being from 1:10,000 to 100:1; or B) the reaction product formed by converting 1) to a catalytically active catalyst by use of an electrochemical oxidation activating technique.

2. A composition according to claim 1 wherein the metal complex corresponds to the formula:

$$(R'')\underset{R''}{\overset{R''}{\diagdown}}\underset{R''}{\overset{R''}{\diagup}})_m M \overset{L_q}{\underset{P'_d}{\diagdown}}$$

wherein:

M is titanium or zirconium in the +2 formal oxidation state;

L is a phosphine or a phosphite group having up to 15 nonhydrogen atoms;

R" is hydrogen, methyl, ethyl, propyl, butyl, pentyl, hexyl, cyclopentyl, cyclohexyl, norbornyl, benzyl, phenyl, or silyl of up to 5 nonhydrogen atoms, or adjacent R" groups are linked together thereby forming an indenyl, tetrahydroindenyl, fluorenyl, tetrahydrofluorenyl, or octahydrofluorenyl group;

P' is pentadienyl, cyclohexadienyl, 6,6-dimethylcyclohexadienyl, silacyclohexadienyl, or 2,4-dimethylpentadienyl;

m, and d are as previously defined in claim 1, and q is 0 or 1.

3. A composition according to claim 1 wherein the metal complex corresponds to the formula:

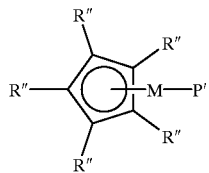

wherein:
M is titanium in the +2 formal oxidation state;
R″ is hydrogen or methyl; and
P′ is 6,6-dimethylcyclohexadienyl, diphenylmethyl, diphenyltrimethylsilylmethyl or 2,4-dimethylpentadienyl.

4. A composition according to claim 1 wherein the activating cocatalyst is selected from the group consisting of polymeric and oligomeric alumoxanes; hydrocarbyl substituted Group 13 compounds containing from 1 to 10 carbons in each hydrocarbyl group; halogenated trihydrocarbylboron compounds containing from 1 to 10 carbons in each halogenated hydrocarbyl group; ion forming compounds selected from the group consisting of compounds represented by the formula:

$$(L^*-H)^+A^-, Ox^{e+}A^-_e, \copyright^+A^- \text{ or } R'_3Si(X')_h{}^+A^-$$

wherein:
L* is a neutral Lewis base;
$A^-$ is a noncoordinating, compatible anion;
$Ox^{e+}$ is a cationic oxidizing agent;
e is an integer from 1 to 3;
$\copyright^+$ is a $C_{1-120}$ carbonium ion;
R′ is $C_{1-10}$ hydrocarbyl;
h is a number from 0 to 3; and
L is as previously defined;
and combinations thereof.

5. A catalyst composition according to claim 1 wherein the activating cocatalyst is methylalumoxane, a $C_{1-30}$ trialkylaluminum compound, a $C_{1-10}$ trihydrocarbylammonium tetrakis (pentafluorophenyl)borate compound, a perfluorinated triarylborane, or a mixture thereof.

* * * * *

UNITED STATES PATENT AND TRADEMARK OFFICE
CERTIFICATE OF CORRECTION

PATENT NO. : 5,990,033
DATED : November 23, 1999
INVENTOR(S) : David R. Wilson et al.

It is certified that error appears in the above-identified patent and that said Letters Patent is hereby corrected as shown below:

Title Page,

Column 2,
Line 2 of Abstract, "containing an anionic" should correctly read -- containing a --.
Line 3, of Abstract, following "pentadienyl" delete ligand --.

Column 22, claim 2,
Line 61, following "silacyclohexadienyl" insert -- diphenylmethyl, diphenyl (trimethylsily)methyl --.

Column 23, claim 3,
Line 15, "diphenyltrimethylsilylmethyl" should correctly read -- diphenyl(trimethylsilyl)methyl --.

Signed and Sealed this

Twenty-first Day of August, 2001

Attest:

NICHOLAS P. GODICI
*Attesting Officer*   *Acting Director of the United States Patent and Trademark Office*